(12) United States Patent
Moret

(10) Patent No.: US 6,699,288 B2
(45) Date of Patent: Mar. 2, 2004

(54) CAGE-TYPE INTERVERTEBRAL IMPLANT

(75) Inventor: Olivier Moret, Sion (CH)

(73) Assignee: Scolio GmbH, Zurich (CH)

( * ) Notice: Subject to any disclaimer, the term of this patent is extended or adjusted under 35 U.S.C. 154(b) by 0 days.

(21) Appl. No.: 09/979,185

(22) PCT Filed: Mar. 21, 2001

(86) PCT No.: PCT/CH01/00179
§ 371 (c)(1),
(2), (4) Date: Mar. 4, 2002

(87) PCT Pub. No.: WO01/70144
PCT Pub. Date: Sep. 27, 2001

(65) Prior Publication Data
US 2003/0100950 A1 May 29, 2003

(30) Foreign Application Priority Data
Mar. 22, 2000 (CH) .................................................... 542/00

(51) Int. Cl.⁷ ..................................................... A61F 2/44
(52) U.S. Cl. ..................................................... 623/17.16
(58) Field of Search ............... 623/16.11, 17.11–17.16; 606/61

(56) References Cited

U.S. PATENT DOCUMENTS

| 4,349,921 A | * | 9/1982 | Kuntz | 623/17.16 |
| 4,904,261 A | * | 2/1990 | Dove et al. | 623/17.16 |
| 5,397,364 A | | 3/1995 | Kozak et al. | |
| 5,425,772 A | * | 6/1995 | Brantigan | 623/17.11 |
| 5,919,235 A | * | 7/1999 | Husson et al. | 623/17.16 |
| 2002/0077700 A1 | * | 6/2002 | Varga et al. | 623/17.11 |
| 2002/0143400 A1 | * | 10/2002 | Biscup | 623/17.11 |

FOREIGN PATENT DOCUMENTS

| EP | 0916323 A1 | 5/1999 |
| EP | 0966929 A2 | 12/1999 |
| FR | 2736537 | 1/1997 |
| WO | 99/65424 | 12/1999 |

* cited by examiner

Primary Examiner—Pedro Philogene
Assistant Examiner—David A Bonderer
(74) Attorney, Agent, or Firm—Burns, Doane, Swecker & Mathis, L.L.P.

(57) ABSTRACT

The invention relates to a cage-type intervertebral implant that is made up of a dished side wall (1), a cambered side wall (2), a front part (3), a rear part (4) and at least one intermediate wall (5, 6), thus comprising at least two cavities (7, 8, 9). An upper and a lower cage surface (10, 11) include a first lordosis angle (α1) in the direction front part—rear part and a second lordosis angle (α2) perpendicular thereto, said cage surfaces (10', 11) intersecting outside the cage. The cage structure is characterized by a double-wedge geometry (double-wedge-shaped cage) that is defined by the two lordosis angles (α1) and (α2) and that advantageously adapts itself to the anatomical conditions in the intervertebral area. The cage is further characterized by a high moment of tilt that effectively counteracts a tipping of the cage. The method used for producing the cage structure is essentially characterized by working the cage material by means of a high-pressure water jet, said cold-cutting technique having proved to be the most economical.

41 Claims, 4 Drawing Sheets

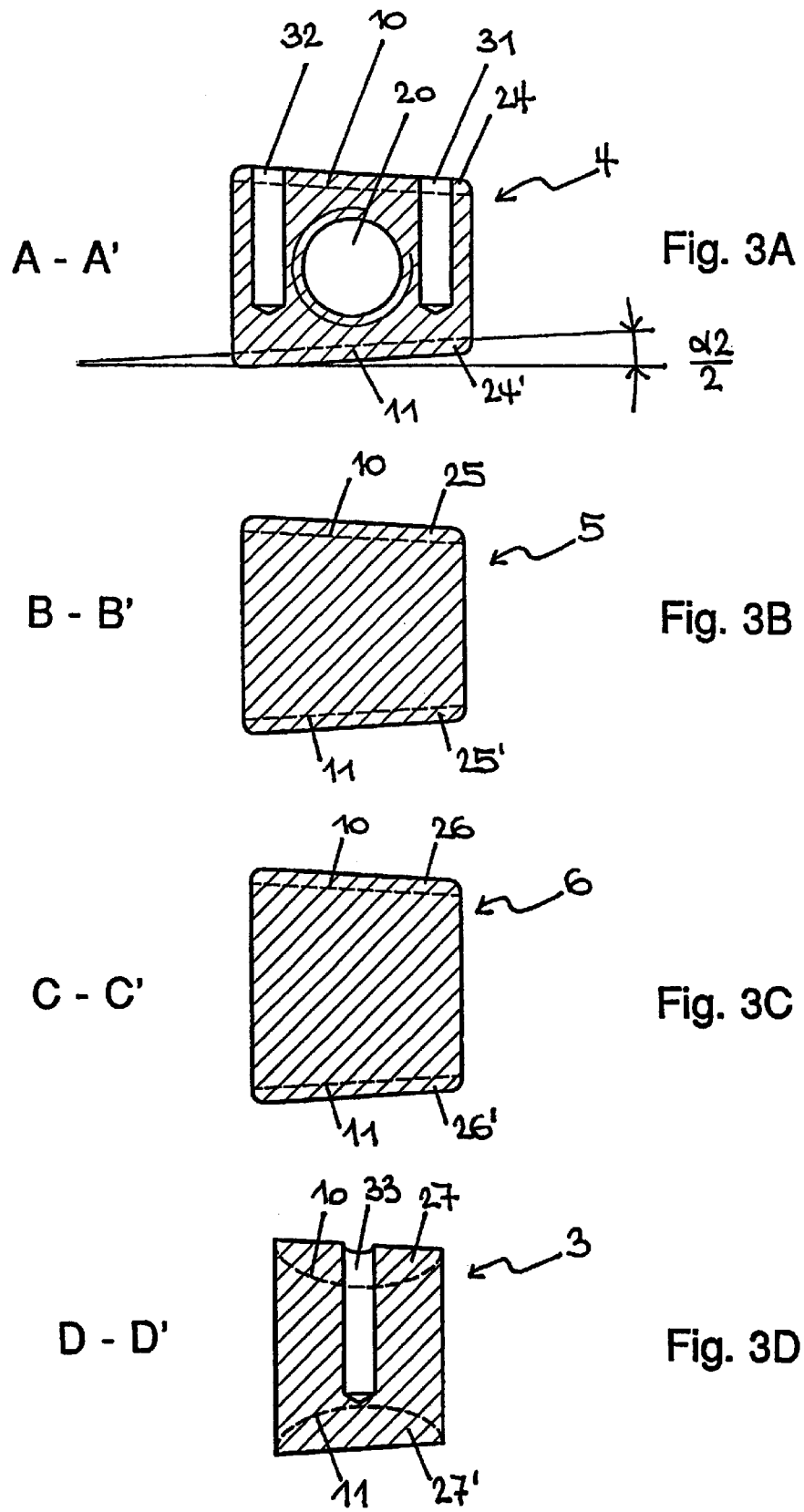

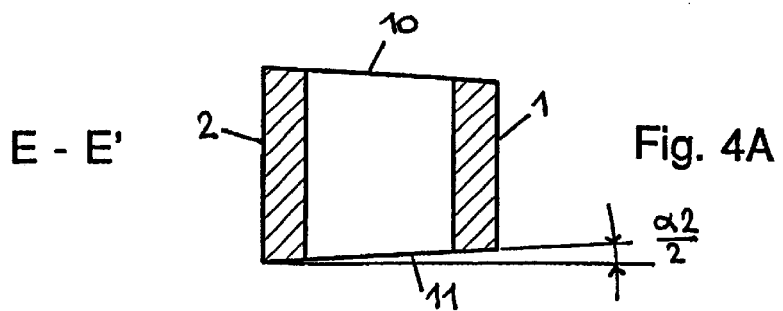
E - E'  Fig. 4A
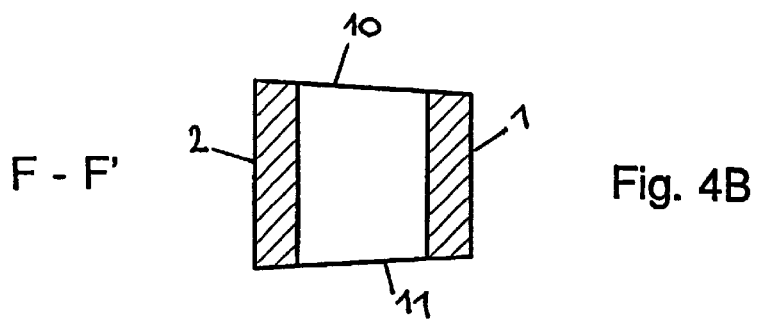
F - F'  Fig. 4B
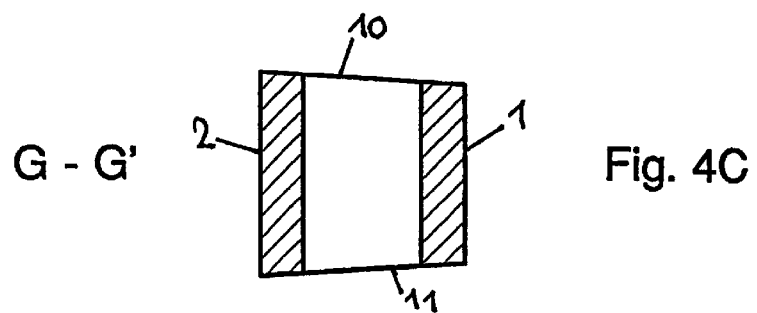
G - G'  Fig. 4C
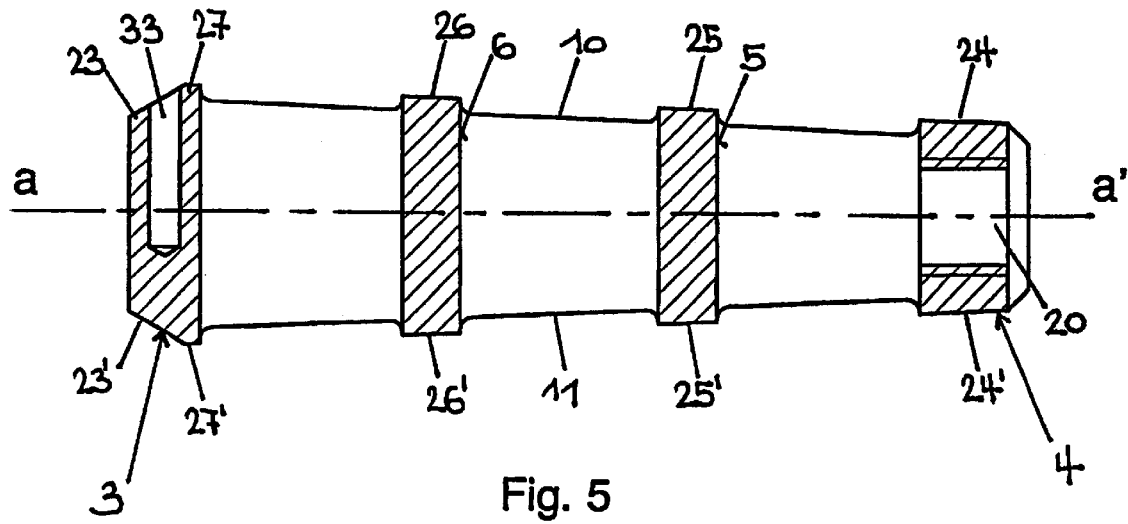
Fig. 5

CAGE-TYPE INTERVERTEBRAL IMPLANT

FIELD OF THE INVENTION

The invention relates to a cage-type intervertebral implant, and also to a method for its production.

It relates to a vertebral column implant and its method of production, the implant being used for insertion between two vertebrae of the vertebral column. It serves as a means of fusion (arthrodesis) of the two vertebral bodies through which the original intervertebral disk height is restored and also the neural foreamen return to their original size.

BACKGROUND OF THE INVENTION

The individual vertebrae of the vertebral column have a vertebral body, a vertebral arch, a spinous process, two transverse processes, and two upper and two lower articular processes. The vertebrae are connected to the abutting intervertebral disks (disci intervertebralis) and give rise to the vertebral body (corpus vertebrae). The intervertebral disk consists of liquid-rich fibrous cartilage and connects the individual vertebral bodies with each other. The size of the intervertebral disks increases from top to bottom, corresponding to the loads arising in the human body. The intervertebral disks serve as elastic buffers and reislently damp impacts.

It is known that the intervertebral disks can become displaced, or that the inner gelatinous core (nucleus pulposus) can emerge through cracks in the cartilaginous outer ring (annulus fibrosus), which is similar to connective tissue. The intervertebral disk can then partially enter the inververtebral foramina (foramina intervertebralia) or into the spinal canal. Furthermore, this prolapse can be dorsal, medial, or lateral. Such prolapses most frequently occur at the L4-L5-S1 and C6-C7 vertebrae. If such prolapses are not treated, irreversible pressure damage of nerve roots, foramina or transverse lesions, result. If physiotherapy according to the symptoms, e.g., remedial exercises or massage, show no promise of success, the intervertebral disk (discuss intervertebralis) has to be surgically removed. There now exist the possibility of implantation of such an implant (cage), by means of which an arthrodesis between the two vertebral bodies can take place.

An intervertebral implant is known from EP 0916323-A1 which has a bean-shaped structure and can be inserted between two vertebrae. The implant has a wedge shape, conferred by a different height of the two longitudinal sidewalls. The walls surrounding the implant are provided with rows of holes in order to promote the ingrowth of bone tissue.

It is disadvantageous that the implant has a wedge shape in only one direction, and is expensive to manufacture because of the many laterally formed holes.

Furthermore, cage structures are known under the designation "Brantigan cage" structures are known which have many teeth on their cage surfaces in order to prevent an undesired displacement of the cage. Made of polyether ether ketone (PEEK), as so-called PEEK moldings, they have inadequate strength, which can lead to breakage of the cage structure under load. A single thread is provided to receive instruments, resulting in unsatisfactory instrument manipulation.

A relatively small moment of tilt is conferred by the cuboidal geometry, with disadvantageous effects.

SUMMARY OF THE INVENTION

The invention has as its object to provide a cage-type intervertebral implant which is characterized by a double wedge geometry defined by two lordosis angles which ensures an improved instrument manipulation.

A further object of the invention consists of the production of such an implant.

According to the invention, this object is attained with an implant according to the wording of patent claim 1 and by a method of production of the same according to the wording of patent claim 23.

BRIEF DESCRIPTION OF THE DRAWINGS

The invention is described herein below using the accompanying drawings:

FIGS. 3A–3D show sectional views of FIG. 2

FIGS. 4A–4C show sectional views of FIG. 2

FIG. 5 is a sectional view of FIG. 2 along the developed radium line 'a–a".

DETAILED DESCRIPTION OF THE INVENTION

Figure 1:
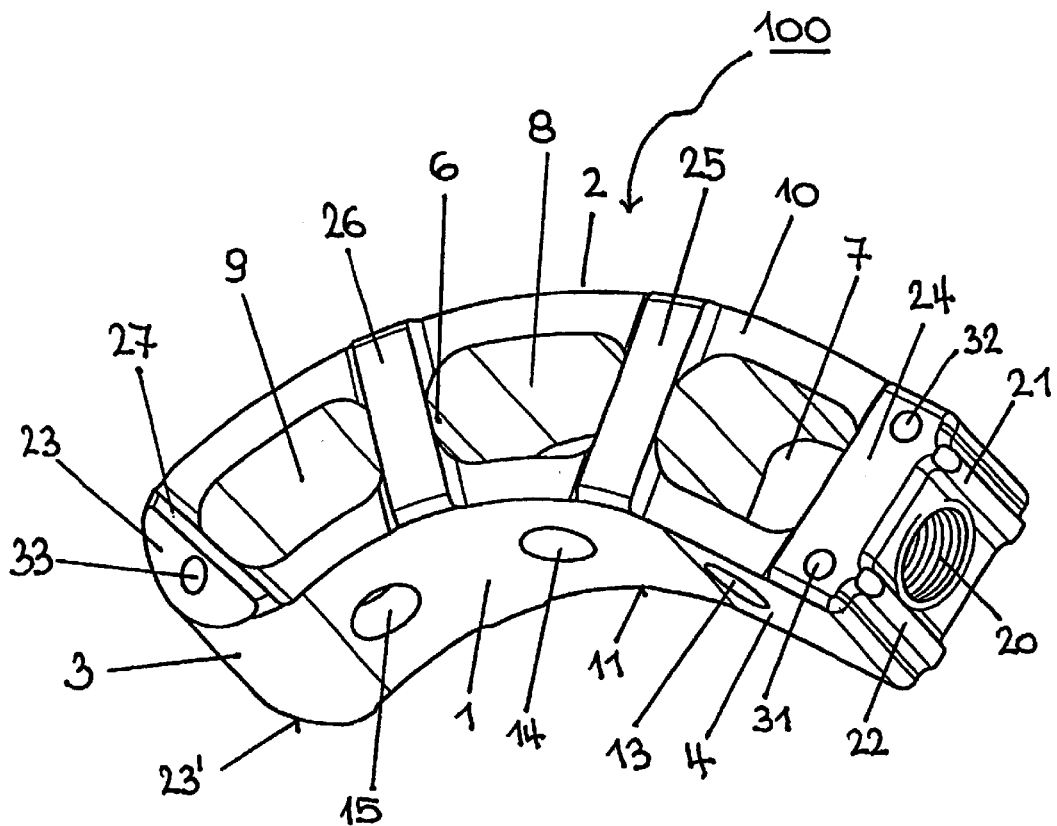
FIG. 1 shows a perspective view of a cage

FIG. 1 shows a cage 100 in a perspective view, consisting of a dished side wall 1, a cambered side wall 2, a front part 3 and a rear part 4. The side walls 1 and 2 are connected by intermediate walls 5 and 6, so that the interior of the cage is divided into cavities 7, 8 and 9. A first, inner, radius of curvature R1 is then allocated to the internal sidewall 1, and a second, outer radius of curvature R2 is allocated to the outer side wall 2.

The side walls 1, 2, the intermediate walls 5, 6, the front part 3 and the rear part 4 have upper, or lower, respective boundaries which define an upper or a lower cage surface.

The dished side wall 1 has rounded openings 13, 14 and 15, which are placed about in the middle of the cavities 7, 8 and 9, and are conducive to the formation of bone substance. The cambered side wall 2 can likewise have such openings (not shown).

The cage surfaces 10, 11 have, in the region of the front part 3, the part 4 and the intermediate walls 5, 6, tabular raised portions 24, 25, 26, 27 which run substantially parallel to the cage surfaces and who properties are described hereinafter.

The front part 3 is rounded, and connects the sidewalls 1, 2 of the cage by means of an equal wall thickness. On the front side it has bevels 23, 23' which facilitate the introduction and positioning of the cage in the intervertebral region.

The rear part 4 is of a rectangular form and connects the sidewalls 1, 2 of the cage, likewise by means of an equal wall thickness. It has a bore 20 on the rear side which is provided with an internal thread and is intended for instrument attachment. Guide elements 21 and 22 are arranged on both sides of the bore 20, and are constituted here as, e.g., ribs, but can also consist of openings in the form of a half cylinder. The guide elements serve to guide instrument introduction, and prevent any improper rotary movement of the cage when the instrument is removed. As soon as the cage is situated in its final position between the two vertebrae, which among other things is the case when the axis of the instrument is perpendicular to the dorsal plane of the patient, the instrument can be detached from the cage. It has become apparent that this possibility of control has turned out to be very helpful and useful.

The transition of the guide elements, or ribs, 21, 22 to the surface of the rear part 4 is rounded off on both sides of the ribs, in order to avoid possible notch effects, which is of importance in embodiments in plastic or composite materials. Holes 31, 32 or 33 are provided in the rear part 4 and in the front part 3, to receive a marker of a high density metal. Tantalum balls and/or pins are particularly suitable for this purpose. The pins are arranged in bores which are arranged either perpendicular or parallel to the bore 20. The position of the cage can thereby be observed and assessed during the operation by means of an image intensifier.

Figure 2:
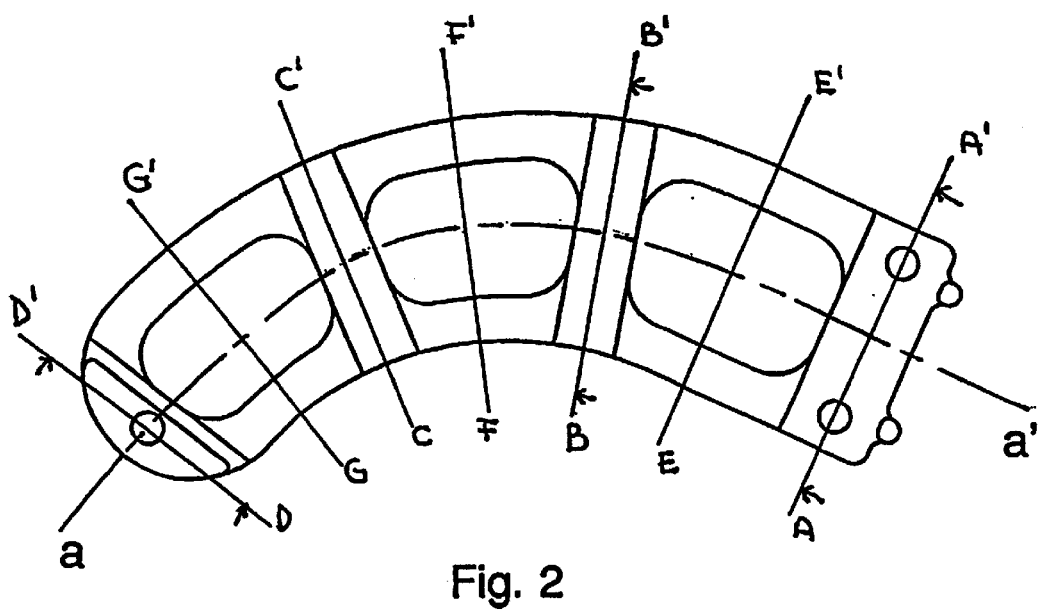
FIG. 2 shows a plan view of the cage according to FIG. 1

FIG. 2 shows a plan view of the cage 100 according to FIG. 1, with data on the position of the sections A–A' through D–D' and E–E' through G–G'. The course of a radius line a–a' which runs through the middle of the cage can likewise be seen.

FIGS. 3A–3D show sectional illustrations of the cage, with section positions according to FIG. 2. FIG. 3A shows a section A–A' through the rear portion 4. The hole 20 to receive an instrument, and the holes 31 and 32 for the markers, are visible. It can furthermore be recognized that the height at the outer side of the rear part is greater than that at the inner side. Thus the upper surface of the rear portion no longer runs parallel to the lower surface, as portions of the cage surfaces 10 and 11. The two surfaces form a lordosis angle $\alpha 2$, which is 0.1–4°, but preferably 2°. This lordosis angle is shown on an exaggerated scale in FIG. 3A, easier recognition. It is shown by $\alpha 2/2$ at the lower side of the rear part.

In the case that the height at the outer side of the rear part is smaller than that at the inner side, there results an opposed slant of the cage, or a wedge shape formed by the case surfaces 10 and 11, with the point of the wedge facing in the reverse direction. If the lordosis angle $\alpha 2$ in the two described cases is identically zero, the cage surfaces 10 and 11 are then parallel, as a special case or borderline case, which of course represents a less preferred design of the cage.

The raised parts 24, 24' are affixed to the parts 10, 11 of the cage surfaces, and here are constituted parallel to the cage surfaces, although this by no means obligatory.

FIGS. 3B and 3C show a section B–B', or C–C', through the intermediate walls 5 or 6, with the raised parts 25, 25', or 26, 26', which are positioned on the parts of the cage surfaces 10, 11. These raised parts again run substantially parallel to the cage surfaces which likewise enable the lordosis angle $\alpha 2$ to be perceived.

FIG. 3D shows a section D–D' through the front part 3. The bore 33 for the marker can be seen. The raised parts 27, 27' can also be seen, which are affixed to the 10, 11 of the cage surfaces of the front part 3. Again, these raised parts run substantially parallel to the cage surfaces, which likewise enable the lordosis angle $\alpha 2$ to be recognized.

The raised parts 24, 25, 26 and 27, which all project from the cage surfaces 10, 11, but are only 0.3–0.8 mm, serve to anchor the cage after the successful operation, and help to prevent a migration of the cage.

FIGS. 4A–4C show sectional diagrams of the cage, with positions of the cross sections according to FIG. 2. There can be seen the sidewalls 1, 2; the upper and lower cage surfaces 10, 11; and the half lordosis angle $\alpha 2$, which is only shown in FIG. 4A on one side.

FIG. 5 shows a sectional diagram of FIG. 2 along the developed radius line a–a'. The hole 33 for the marker, the bevels 23, 23', and the raised portions 27, 27' can be seen in the front part 3; the hole 20 and the raised portions 24, 24' can be seen in the rear part 4. The intermediate walls 5, 6 respectively have the raised parts 25, 25' or 26, 26'.

It can further be seen that the height of the front part 3 is greater than that of the rear part 4. Thus the case surfaces 10 and 11 no longer run parallel. The two surfaces form a so-called lordosis angle $\alpha 1$, which is 2–8°, but preferably 3°, 5°, or 7°. This non-parallelism conditioned by the lordosis angle $\alpha 1$ is shown on an exaggerated scale to FIG. 5, to be more easily visible.

The cage structure can of course be modified within wide limits within the scope of this invention. Thus, for example, the number of the intermediate walls 5, 6, or that of the cavities 7, 8, 9, or that of the cavities 7, 8, 9 is not limited to 2 or 3. Cage structures with one or more intermediate walls are possible.

Figure 6A:
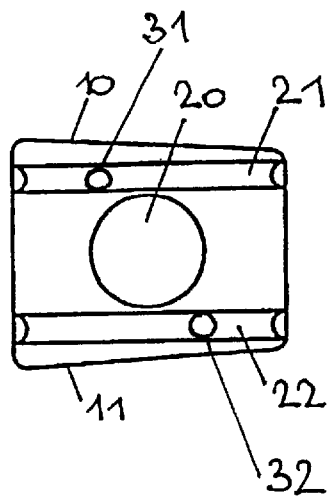
FIGS. 6A–6B show side views of the rear portion with differently arranged guide elements
Figure 6B:
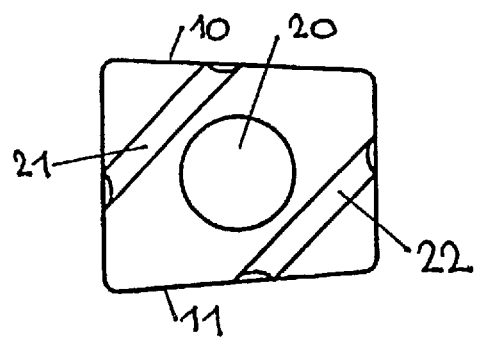

FIGS. 6A and 6B each show a side view of the rear part with different guide elements 21 and 22 arranged around the hole 20.

In FIG. 6A, the guide elements are arranged approximately parallel to the cage surfaces 10, 11, while those in FIG. 6B have an angle of about 45° to the cage surfaces. However, this angle can assume any value from 0 to 90°. The guide elements 21, 22 in their turn of course do not necessarily have to be arranged parallel to one another; they can also have a V-shaped arrangement.

Possible materials are plastics, carbon fiber reinforced plastics and metals or metal alloys. Plastics such as polyether ether ketone (PEEK), polyether ketone ether ether ketone (PEKEEK) and polysulfone (PS) are preferably used, and particularly preferred as composite materials, carbon fiber reinforced composites of polyether ether ketone (CFK/PEEK) and polyether ketone ether ketone ketone (PEKEEK), which are also known under the names of ULTRAPEK and OSTAPEK.

As metals or metal alloys, titanium and its alloys are preferably used, such as e.g., the titanium alloy Ti6-Al4-V according to ISO standard 5832-3.

The metallic cage can have a hydroxyapatite ceramic (HAK) coating or a tricalcium phosphate (TCP) coating, which advantageously affect the long-term properties of the implant.

The curved shape of the cage gives this an advantageous high tilting moment M, which effectively counteracts a tipping of the cage. In comparison with the moment of tilet of a cuboidal cage with equal middle cross section, equal length, and comparable cage structure, it has been found that the cage structures according to the invention exceed this by a factor of at least 1.30. For a cage according to FIG. 1, the factor is 1.58.

The advantages of the cage structure according to the invention result from the double-wedge geometry, which is defined by the two lordosis angles $\alpha 1$ and $\alpha 2$, and that advantageously adapts itself to the anatomical condition in the intervertebral area.

The designation "double wedge-shaped cage" or "DWS cage" is therefore used for such a cage.

The raised portions positioned on the cage surfaces effectively prevent a migration of the cage during the healing process after a successful operation.

Cage structures of the described kind are distinguished by high strength attained in spite of a small proportion of material. The formation of bone material is thereby strongly accelerated.

It has been found that this property can be described by a Cage Mass Index (CMI), which is defined according to Equation (1), CMI=Volume of cage material/Volume of cage    (1)

namely as the ratio of the cage material volume to the total cage volume. The results are:

(a) for CFK/PEEK, CFK/PEKEKK, CFK/PS less that 0.25, preferably 0.22, and (b) for titanium or Ti alloys, less that 0.20, preferably 0.17, whereby the variations dependent on the on the cage sizes are taken into account and result in only unimportant difference.

The process for the production of such a cage is described hereinafter. It is divided into of four process steps, as follows:

1. Water Jet Cutting

In a first step, a blank of cage material is machined in a first direction by means of a high pressure water jet. This known and economical cold cutting process is as a rule operated with an abrasive addition at 3,000 bar (U. W. Hunziker-Jost, Swiss Precision Manufacturing Technique, p. 81–86, C. Hanser Verlag, Munich (1991)).

The blank is clamped so that the water jet is directed perpendicularly to the later cage surface. The contours of the sidewalls 1, 2, of the front part 3, of the rear part 4, of the at least one intermediate wall 5, 6, of the at least two cavities 7, 8, 9, and of the guide elements 21, 22 are cut with high precision. The cut edges display little fraying. With material thicknesses of 10 mm, cutting speeds are attained of up to 100 mm/min for metals and up to 300 mm/min for composite materials 2. Milling The cage blank cut from the blank in this manner is now clamped again in a second step, and in fact in a second direction, essentially perpendicular to the first direction, in which the cage blank is further machined with a miller. The surfaces milled are the cage faces 10, 11 corresponding to the lordosis angle α1, the wedge-shaped raised portions 24, 25, 26, 27 corresponding to the second lordosis angle α2, the beveled surfaces 23, 23' of the front part 3, the at least one opening of the side walls 1, and the first hole 20. Likewise in this step, the hole 20 is provided with an internal thread, which is intended to receive an instrument. Small-calibered milling inserts are used here on a CNC-steered automatic milling machine.

If openings are likewise to be provided in the outer sidewall 2, the cage blank has to be newly clamped once more.

3. Affix Markers

In a third step, the markers are mounted on the cage blank; later, during the operation and thereafter, they make it possible to assess the position of the cage by means of an image intensifier. Second holes 31, 32, 33 are installed for the markers in the rear portion and the markers in the front portion, and the markers are inserted into them as tantalum balls and/or pins.

4. Finishing

In a fourth step the last operations, summarized as finishing, take place, namely trovalization in order to deburr or round off the partially sharp edges. Then follows the marking of the cage, which can be done by means of a laser marking device. The cage is next subjected to a cleaning process, which includes, for example, multi-step ultrasonic cleaning. The packaging of the cage likewise belongs to these finishing operations.

An important process step is cutting with a high-pressure water jet. An advantageous cutting process was thereby selected, which has proven to be particularly economical.

The examples described hereinafter give an insight into the diversity of the cage design, and their enumeration is not to be considered as final in any way.

Figure 7:
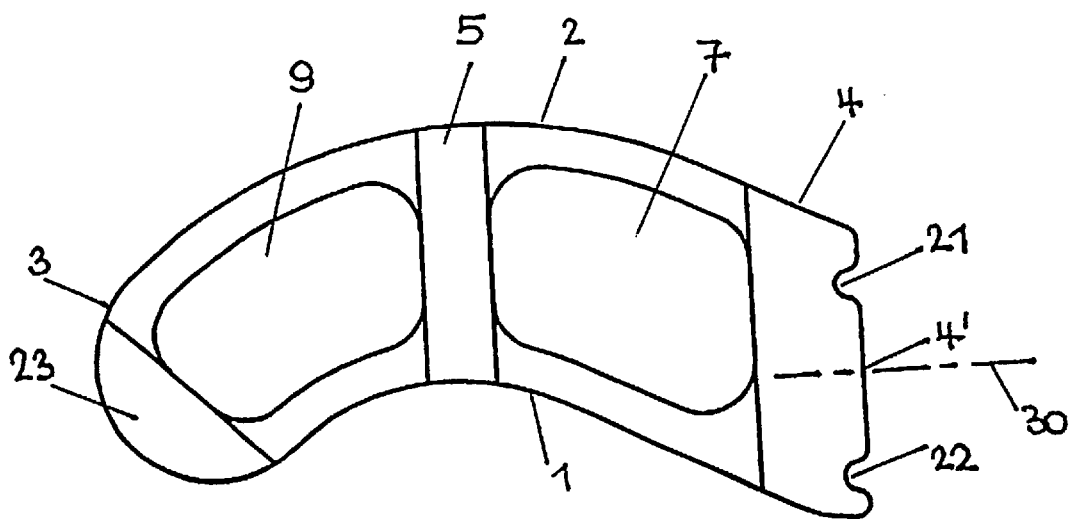
FIG. 7 is a plan view of an embodiment example of a cage with a partition and oblique rear portion with openings.

FIG. 7 shows in plan view, as an embodiment example, a cage with one intermediate wall and an oblique rear part with openings.

Side walls 1, 2, front part 3 with raised portion and bevel 23, intermediate wall 5 with raised part, and the cavities 7, 9, correspond to the cage elements described in FIG. 1. The rear part 4 with a part raised with respect to the cage surface has here, however, a rhomboidal constitution. While the guide elements 21, 22 are constituted as recesses here, but are arranged on the rear part surface 4' as in FIG. 1, the direction of the hole for receiving an instrument is shown at the edge of the cavity 7 by the position of the axis 30 for the hole. The hole is provided with an M4 internal thread.

The cage surfaces form a lordosis angle α1 of 3° in the front part—rear part, and a lordosis angle α2 of 2° in the direction of the centers for the curvature radii of the curved side walls 1 and 2. Thus the height of the intermediate wall with raised part is 8.1 mm on the outer side and 7.8 mm on the inner side. The side wall 1 has two lateral openings which are situated about in the middle of the cavities 7 and 9. The inner radius of curvature R1 is 11 mm, and the outer radius of curvature R2 is 19 mm, the respective centers being 1.1 mm apart. The cage was made of CFK/PEEK, a BYJET water jet cutting apparatus (Bystronic Laser AG, CH-3362 Niederönz) being used in the first process step.

As a further embodiment example, the cage structure according to FIG. 6 was manufactured from a titanium alloy, Ti6-Al4-V according to ISO Standard 5832-3, a BYJET water jet cutting apparatus likewise being used in the first process step.

What is claimed is:

1. A cage for a cage-like intervetebral implant, comprising a member divided into cavities, wherein the cage comprises a dished inner side wall, a cambered outer side wall, a front part, and a rear part, a first, inner readius of curvature being allocated to the dished inner wall, and a second, outer radius of curvature being allocated to the cambered outer side wall; the side walls are connected to the front part and the rear part; the side walls are connected to at least one intermediate wall substantially perpendicular to the side walls, whereby the cage has at least two cavities; and the side walls, the front part, the rear part, and at least one intermediate wall form an upper and a lower cage surface, a first lordosis angle being formed between said upper and lower cage surfaces in a front part—rear part direction such that said upper and lower cage surfaces are not parallel to each other in said front part—rear part direction, and second lordosis angle being formed between said upper and lower cage surfaces in an outer side wall—inner side wall direction perpendicular to said front part—rear part direction such that said upper and lower cage surfaces are not parallel to each other in said outer side wall—inner side wall direction.

2. A cage according to claim 1, wherein the inner side wall has a smaller height than the outer side wall, or the outer sidewall has a smaller height than the inner sidewall.

3. A cage according to claim 1, wherein the front part and the rear part have a substantially equal second lordosis angle.

4. A cage according to one of claims 1, wherein the first lordosis angle is 2° and 8°.

5. A cage according to claim 4, wherein the first lordosis angle is 3°.

6. A cage according to claim 4, wherein the first lordosis angle is 5°.

7. A cage according to one of claims 4, wherein first lordosis angle is 7°.

8. A cage according to claims 1, wherein the second lordosis angle is between 0.1° and 4°.

9. A cage according to claims 1, wherein the first, inner radius of curvature and the second, outer radius of curvature have centers arranged offset to one another.

10. A cage according to claim 1, wherein the inner radius of curvature is between 15 and 23 mm and the outer radius of curvature is between 18 mm and 26 mm.

11. A cage according to claim 1, wherein the inner side wall has a least one opening.

12. A cage according to claim 1, wherein the outer side wall has a least one opening.

13. A cage according to claim 1, wherein the front part is rounded and has a least one beveled surface.

14. A cage according to claim 1, wherein holes are provided in the front part and in the rear part for markers of a metal of high density, said markers comprising at least one of balls and pins.

15. A cage according to claim 14, wherein tantalum is provided as the metals for the markers.

16. A cage according to claim 14, wherein the markers are arranged as pins that are one of approximately perpendicular or parallel to a threaded hole.

17. A cage according to claim 14, wherein said markers are pins and the pins are parallel to a threaded hole.

18. A cage according to claim 1, wherein the cage surfaces have tabular raised portions which run substantially parallel to the cage surfaces.

19. A cage according to claim 1, wherein the cage has a moment of tilt (M) directed in the direction of the center of the inner radius of curvature that is at least 1.30 times greater than the moment of tilt of a cuboidal cage of the same cross section, same length and comparable cage structure.

20. A cage according to claim 1, wherein the cage comprises carbon fiber reinforced composites of CFK/PEEK and CFK/PEKEKK.

21. A cage according to claim 1, wherein the cage comprises a Ti alloy.

22. A cage according to claim 21, wherein said cage has one of a hydroxyapatite ceramic (HAK) coating or a tricalcium phosphate (TCP) coating.

23. A cage according to claim 1, wherein said cage has a Cage Mass Index (CMI) according to Equation $$CMI = \text{Volume of cage material} / \text{Volume of cage} \qquad (1)$$

which for CFK/PEEK, CFK/PEKEKK, and CFK/PS is less that 0.25 and for Ti alloys, is less thatn 0.20.

24. A cage according to claim 23, wherein a CMI for CFK reinforced PEEK, a CMI for CFK reinforced PEKEKK and a CMI for CFK reinforced PS is equal 0.22.

25. A cage according to claim 23, wherein a CMI for titanium alloy is equal 0.17.

26. A cage for a cage-like intervertebral implant, comprising a member divided into cavities, wherein the cage comprises a dished inner side wall, a cambered outer side wall, a front part, and a rear part, a first, inner radius of curvature being allocated to the dished inner side wall, and a second, outer radius of curvature being allocated to the cambered outer side wall; the side walls are connected to the front part and the rear part; the side walls are connected to at least one intermediate wall substantially perpendicular to the side walls, whereby the cage has at least two cavities; and the side walls, the front part, the rear part, and the at least one intermediate wall form an upper and a lower cage surface, a first lordosis angle being formed between said upper and lower cage surfaces in a front part—rear part direction such that said upper and lower cage surfaces are not parallel to each other in said front part—rear part direction, and a second lordosis angle being formed between said upper and lower cage surfaces in an outer side wall—inner wall direction perpendicular to said front part—rear part direction such that said upper and lower cage surfaces are not parallel to each other in said outer side wall—inner side wall direction, wherein the rear part has in its middle a hole with an internal thread, which is surrounded by two guide elements which run substantially parallel or in a V-shape.

27. A cage according to claim 26, wherein the guide elements are arranged at one of approximately perpendicular, or about parallel, or at an angle of 0° to 90° to the cage surfaces around the threaded hole.

28. A cage according to claim 26, wherein the internal thread is surrounded by recesses which run substantially parallel or in a V-shape.

29. A cage according to claim 26, wherein the two guide elements are in a V-shape.

30. A cage according to claim 26, wherein the guide elements are arranged approximately parallel to the cage surfaces around the hole.

31. A cage according to claim 26, wherein the guide elements are arranged approximately at an angle between 0° and 90° to the cage surfaces around the hole.

32. A cage according to claim 26, wherein the guide elements are arranged approximately at a 45° angle to the cage surfaces around the hole.

33. A cage for a cage-like intervertebral implant, the cage comprising:

a member divided into cavities;

a concave-curved inner sidewall having a first inner radius of curvature;

a convex-curved outer sidewall having a second outer radius of curvature;

a front portion;

a rear portion where both the concave-curved sidewall and the convex-curved sidewall are connected to the front portion and the rear portion, the concave-curved sidewall and the convex-curved sidewall being connected to a least one partition substantially perpendicular to both the concave-curved sidewall and the convex-curved sidewall to form a cage with at least two cavities wherein the concave-curved sidewall, the convex-curved sidewall, the front portion, the rear portion and the at least one partition forms an upper cage surface and a lower cage surface where the upper cage surface and the lower cage surface form a first lordosis angle in a front portion—rear portion direction such that the upper cage surface and a lower cage surface are not parallel to each other in the front portion—rear portion direction and the upper cage surface and the lower cage surface form a second lordosis angle in a concave-curved sidewall—convex-curved sidewall direction such that the upper cage surface and the lower cage surface are not parallel to each other in the concave-curved sidewall—convex-curved sidewall direction.

34. A cage according to claim 33, wherein the outer sidewall has a smaller height that the inner sidewall to form the second lordosis angle.

35. A cage according to claim 33, wherein the second lordosis angle is 2°.

36. A cage according to claim 33, wherein a center of the first inner radius of curvature is offset from a center of the second outer radius of curvature.

37. A cage according to claim 33, wherein the first inner radius of curvature is 22 mm.

38. A cage according to claim 33, wherein the second outer radius of curvature is between 18 mm and 26 mm.

39. A cage according to claim 33, wherein the second outer radius of curvature is 19 mm.

40. A cage according to claim 33, wherein the second outer radius of curvature is 21 mm.

41. A cage according to claim 33, wherein the second outer radius of curvature is 23 mm.

* * * * *